United States Patent
Itu et al.

(10) Patent No.: US 10,984,905 B2
(45) Date of Patent: Apr. 20, 2021

(54) ARTIFICIAL INTELLIGENCE FOR PHYSIOLOGICAL QUANTIFICATION IN MEDICAL IMAGING

(71) Applicant: Siemens Healthcare GmbH, Erlangen (DE)

(72) Inventors: Lucian Mihai Itu, Brasov (RO); Puneet Sharma, Princeton Junction, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 471 days.

(21) Appl. No.: 15/957,356

(22) Filed: Apr. 19, 2018

(65) Prior Publication Data

US 2019/0139641 A1    May 9, 2019

Related U.S. Application Data

(60) Provisional application No. 62/581,071, filed on Nov. 3, 2017.

(51) Int. Cl.
  *G16H 30/20*   (2018.01)
  *G16H 10/60*   (2018.01)
  *G06N 3/08*    (2006.01)
  *G16H 50/20*   (2018.01)

(52) U.S. Cl.
  CPC .............. *G16H 30/20* (2018.01); *G06N 3/08* (2013.01); *G16H 10/60* (2018.01); *G16H 50/20* (2018.01)

(58) Field of Classification Search
  CPC ........ G16H 30/20; G16H 50/20; G16H 10/60; G06N 3/08; G06N 3/0427; G06N 20/10; G06N 5/003; G06N 7/005; G06N 20/20; G06N 5/025; G06N 3/0472; G06N 3/0454
  See application file for complete search history.

(56) References Cited

U.S. PATENT DOCUMENTS

| | | | |
|---|---|---|---|
| 2016/0196384 A1* | 7/2016 | Mansi ................. | G06F 19/321 600/301 |
| 2017/0337682 A1* | 11/2017 | Liao ......................... | G06T 7/30 |
| 2017/0357844 A1 | 12/2017 | Comaniciu et al. | |

OTHER PUBLICATIONS

Hasan, Ali and Boyce Griffith. Patient specific hemodynamic modeling of the aortic root. University of North Carolina Chapel Hill Math Department, Honors Thesis. (Year: 2017).*
Itu, L. M., Sharma, et al., "Model Based Non-invasive Estimation of PV Loop from Echocardiography" Proc. of the 36th Annual Inter. Conf. of the IEEE Engineering in Medicine & Biology Society—EMBC 2014, Chicago, USA, Aug. 26-30, 2014, pp. 6774-6777.
Bishop CM. Pattern recognition and machine learning. New York, NY: Springer, 2006.

(Continued)

*Primary Examiner* — Linh Giang Le

(57) ABSTRACT

For quicker estimation of physiological parameters than using a numerical solution, a machine-learned network is applied. The PV loop may be estimated for a specific patient in real-time without invasive pressure measurements. Synthetic data instead of or in addition to actual patient examples may be used to machine train the network, providing a broader and/or controlled range of examples for more accurate estimation even in rarely occurring pathologies. The synthetic data may be generated by a generative adversarial network.

20 Claims, 4 Drawing Sheets

(56) References Cited

OTHER PUBLICATIONS

Chen, Xi, et al. "Infogan: Interpretable representation learning by information maximizing generative adversarial nets" Advances in Neural Information Processing Systems. 2016.

Chinali M. et al. Patient-Specific Heart Model in Children with Dilated Cardiomyopathy: a Useful Tool to Guide Beta-Blocker Therapy in Children with Heart Failure, VPH conference, Amsterdam, 2016.

D. Burkhoff, "Pressure-Volume Loops in Clinical Research: A Contemporary View," Journal of the American College of Cardiology, vol. 62, pp. 1173-1176, 2013.

D. M. Spevack, et al, "Echocardiographic left ventricular end-diastolic pressure volume loop estimate predicts survival in congestive heart failure," Journal of Cardiac Failure, vol. 19, pp. 251-259, 2013.

F. J. Van Slochteren, et al, "Left ventricular PV loop estimation using 3D echo", 2012; Eindhoven University of Technology, Internal report BMTE 07.42, Accessible at: http://www.mate.tue.nl/mate/pdfs/8738.pdf.

Goodfellow, Ian, et al. "Generative adversarial nets." Advances in neural information processing systems. 2014.

\* cited by examiner

Specify initial set of input data:
- pressure measurements (SBP, DBP)
- heart rate
- left ventricular volume values (min / max)
- duration of systole
- type of LV volume curve (e.g. with / without diastolic plateau)
FIG. 5A
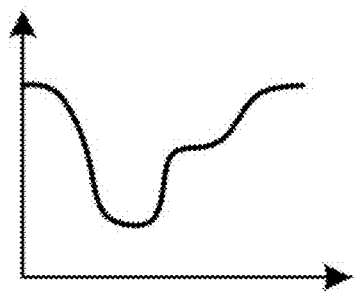
Generate volume curve
FIG. 5B
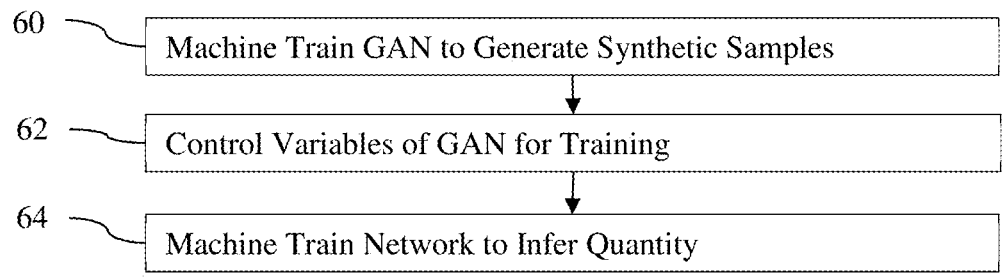
FIG. 6
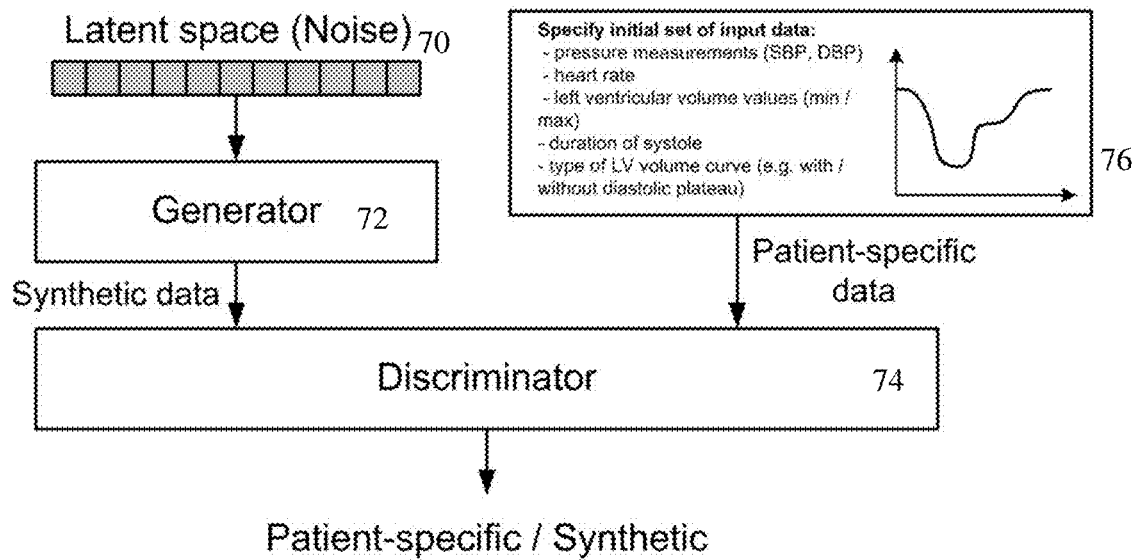
FIG. 7

ARTIFICIAL INTELLIGENCE FOR PHYSIOLOGICAL QUANTIFICATION IN MEDICAL IMAGING

RELATED APPLICATIONS

The present patent document claims the benefit of the filing date under 35 U.S.C. § 119(e) of Provisional U.S. Patent Application Ser. No. 62/581,071, filed Nov. 3, 2017, which is hereby incorporated by reference.

BACKGROUND

The present embodiments relate to medical imaging, such as medical imaging of the cardiac system of a patent. The left ventricular (LV) pressure-volume (PV) loop represents an efficient tool for understanding and characterizing cardiac function. The PV loop contains information regarding stroke volume, cardiac output, ejection fraction, myocardial contractility, cardiac oxygen consumption, and other important measures of the heart and the systemic circulation. For example, the PV loop indicates the extent of ventricular remodeling, the degree of ventricular-arterial mismatching, and the left ventricular end-diastolic pressure-volume relationship, which represent strong predictors of congestive heart failure. Pathologies such as left ventricular hypertrophy, dilated cardiomyopathy, aortic and mitral valve stenosis, and regurgitation are manifested in the PV-loop. Other quantities may predict other conditions.

Medical imaging modalities such as magnetic resonance imaging (MRI), computed tomography (CT), and echocardiography can be used to estimate the time-varying LV volume through the heart cycle in a non-invasive manner, which can then be combined with an invasive measurement of LV pressure to obtain the PV loop. This invasive approach is expensive and associated with increased patient risks. Alternatively, model-based approaches may be employed for the non-invasive estimation of left ventricular, patient-specific PV loops. A lumped parameter circulation model, personalized using a two-step parameter estimation framework may be used to estimate the PV loop. The input data required for the model personalization is acquired through routine non-invasive clinical measurements and echocardiography. Other physiological models combine geometrical information extracted from medical imaging with background knowledge on the physiology of the system encoded in a complex mathematical model of ordinary or partial differential equations, which can be solved only numerically. This approach leads to a large number of algebraic equations, making it computationally very demanding. It may take minutes or hours to determine the PV loop using these models. Minutes or hours is not desired during diagnosis and may not be sufficient during a procedure. The computationally demanding aspect of these models and associated image segmentation process prevents adoption of this technology for real-time applications, such as intra-operative guidance of interventions.

SUMMARY

By way of introduction, the preferred embodiments described below include methods, computer readable media and systems for physiological quantification. For quicker estimation of physiological parameters than using a numerical solution, a machine-learned network is applied. The PV loop may be estimated for a specific patient in real-time. Synthetic data instead of or in addition to actual patient examples may be used to machine train the network, providing a broader and/or controlled range of examples for more accurate estimation even in rarely occurring pathologies. The synthetic data may be generated by a generative adversarial network.

In a first aspect, a method is provided for physiological quantification in a medical system. Medical scan data representing anatomy of a patient is acquired. A machine applies the medical scan data or features from the medical scan data to a machine-trained estimation network. The machine-trained estimation network was trained, at least in part, from synthetic data generated by a generator of a machine-trained generative adversarial network. The synthetic data is not specific to existing patient cases. Due to the application to the machine-trained estimation network, a pressure-volume loop is determined for the patient within a second of the acquisition of the medical scan data. The pressure-volume loop is output.

In a second aspect, a method is provided for machine training for synthetic data generation in a medical system for quantification. A machine trains a generative adversarial network to generate synthetic data by a generator representing various instances of anatomy based on a plurality of samples of anatomy of patients and feedback from a discriminator. The machine trains a quantification network to infer a physiological quantity. The quantification network is trained based on the synthetic data from the generative adversarial network.

In a third aspect, a system is provided for physiological quantification. A medical imaging scanner is configured to scan a patient. An image processor is configured to apply information from the scan to a machine-learned network. The machine-learned network is configured by training to output a pressure volume loop in response to the application of the information. The output is in real-time with the scan. A display is configured to display the pressure volume loop.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

FIGS. 5A and 5B show a representation of a two-step process for generating synthetic data from the lumped model of FIG. 3;

FIG. 6 is a flow chart diagram of one embodiment of a method for machine training including training for synthetic data generation in a medical system for quantification;

FIG. 7 illustrates an example generative adversarial network for learning to generate synthetic data;

DETAILED DESCRIPTION OF THE DRAWINGS AND PRESENTLY PREFERRED EMBODIMENTS

Figure 1:
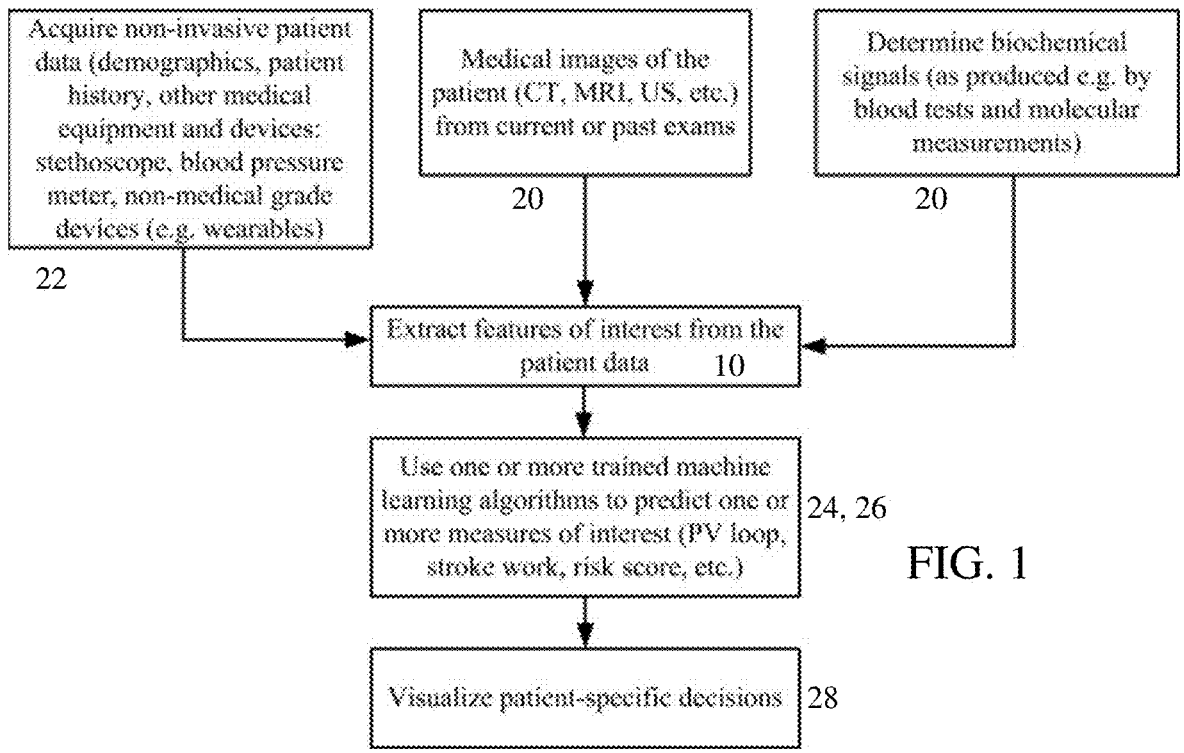
FIG. 1 is a flow chart of one embodiment of a method for physiological quantification in medical imaging.

The collection of data from patient images and measurements presents a very complex network of information about the patient. This complex network of information may be effectively untangled by modern machine learning algorithms. A machine-learned network provides fast patient assessment. Machine learning and artificial intelligence algorithms are well suited to managing large quantities of heterogeneous data. Consistent estimations are provided in an automated manner. Machine learning algorithms have superior predictive capabilities in complex tasks, showing expert-level performance.

Artificial intelligence is used for advanced physiological quantification, such as real-time PV loop computation. Advanced physiological quantification uses artificial intelligence techniques, such as a machine learning algorithm trained and applied to predict physiological quantities of interest like the PV loop, stroke work, and/or a risk score. For application of the machine-learned network, medical data (e.g., imaging and/or non-imaging) is acquired from the patient. The artificial intelligence (AI)-based model is run on the available input data to perform real-time advanced physiological quantification, such as to generate a PV loop. The results may be visualized. Another AI-based model may provide a clinical decision (e.g. send patient for further exams or discharge) based on the available patient data and the measures of interest generated by the first AI model. Yet another AI-based model may predict the evolution of the patient and/or evolution of certain clinical measures of interest. A multi-task AI-based model may be developed, performing the functions of any combination of the above mentioned three AI models. Any of the AI-based models may use measurements acquired from wearable devices. Any of the AI-based models may be run at different time points, using the continuous measurements from wearable devices as input data, such as to assess the patient evolution and take further decisions (e.g. regarding next clinical exam).

The physiological quantification, such as a PV loop, is generated in real-time since AI-based techniques are employed. Rather than quantifying with physiological or computational models requiring longer runtimes, values may be provided within seconds of having completed scan of the patient. This efficient estimation of the PV loop represents a powerful diagnostic tool for clinicians. Since the AI-based approach is used, the PV loop may be predicted for different patient states, being employed to perform enhanced personalized and precise diagnosis of the patient and the pathologies and even predict the future evolution of the patient.

To handle a broader range of patients and/or pathologies in light of the many samples used in machine training, synthetic data is used for training. The synthetic data is used without patient-specific samples, but patient-specific samples may be used instead or in addition to synthetic data. Synthetic examples may be used to augment the training database. In one embodiment, a Generative Adversarial Network (GAN) is trained from samples from patients to generate synthetic data, providing additional samples for training. Synthetic generated training data have various advantages over collecting patient examples. A very large number of cases can be automatically generated, leading thus to an extensive database for training, which results in greater accuracy of inference. Complex pathological configurations can be generated. Since the generation of synthetic in-silico geometries can be completely automated, the cost of generating a large database is reduced as compared to collecting actual patient cases. Rare pathological cases may be sampled better. The training data may be extended to different demographic groups easily. The training can be done in a global manner or a site-specific manner. This allows the system to account for anatomical trends based on patient demographics and epidemiology. The training can be iteratively improved with either more data, or with better representations of the features provided by any improvement in the models used to generate the synthetic data.

Figure 2:
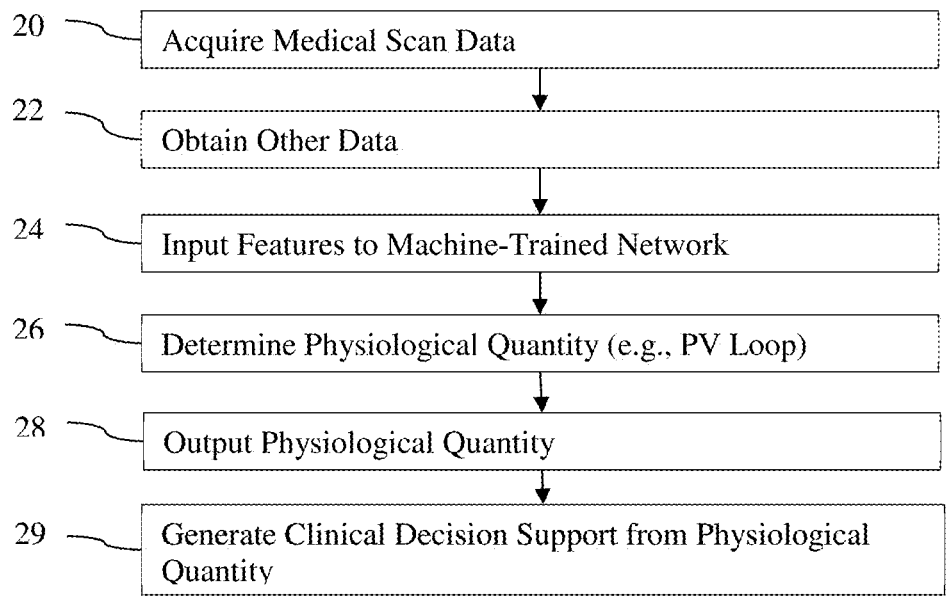
FIG. 2 is a flow chart of an embodiment of a method for physiological quantification by a medical system.

FIGS. 1 and 2 are flow chart diagrams of embodiments of a method for physiological quantification in a medical system. A machine-learned network is applied to output a physiological quantification. FIG. 1 shows a generic workflow for predicting one or more physiological quantities. One or more trained machine learning model(s) provide real-time values for the quantities and/or are configured by having been trained with synthetic data from a GAN. FIG. 2 is an example of FIG. 1 where deep learning is used so that the feature extraction of act 10 is performed by input of the scan and other data to the machine-learned network.

Figure 10:
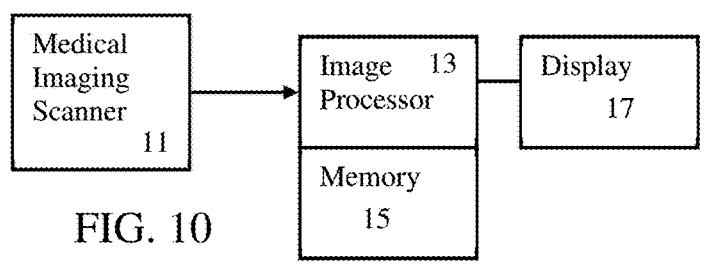
FIG. 10 is a block diagram of one embodiment of a medical system for physiological quantification.

The medical system of FIG. 10 or other medical system implements the acts. The system may be a medical imaging system, a hospital workstation, a patient medical records computer, a medical server, a cloud-based system, or other secure medical data processing system. The medical system may or may not include a memory or database, such as patient medical record database, oncology data from oncology information system, and/or picture archiving and communications system (PACS).

The acts of FIGS. 1 and 2 are performed in the order shown (numerical or top to bottom) or other orders. For example, acts 20 and 22 occur simultaneously or in any order. As another example, act 10 may be performed as part of act 24, such as where a deep-learned classifier is used.

Additional, different, or fewer acts may be provided. For example, acts 28 and/or 29 may not be performed. As another example, act 22 or act 20 is not performed. Example additional acts include input of features to other machine-learned networks, configuration of the machine for patient-specific application, and/or other uses of the output quantification.

In act 20, a medical system acquires medical scan data. The medical scan data is acquired by loading from memory. Alternatively or additionally, the medical scan data is acquired by a medical imaging scanner, such as an x-ray, computed tomography (CT), magnetic resonance imaging (MRI), molecular imaging (e.g., positron emission tomography (PET) or single photon emission computed tomography (SPECT)), ultrasound, camera, or another scanner. The medical imaging scanner is part of or is the medical system, or the medical system acquires the scan data by transfer from the imaging scanner over a computer network.

The medical scan data is acquired for a given patient for diagnosis, prognosis, and/or therapy. The medical scan data represents a one, two, or three-dimensional region of the patient. For example, in 3D imaging using any of different modalities, a set of scan data representing intensity at different voxels distributed over three dimensions is acquired. In other embodiments, the medical scan data is two-dimensional representation of a plane or projection through the patient. The medical scan data or image data may be data formatted prior to imaging (e.g., voxels) and/or data formatted as an image for display (e.g., a multi-planar reconstruction or volume rendering).

The medical scan data represents anatomical structures of the patient or patients. Any anatomy may be represented, such as part of the heart or circulatory system or, alternatively, whole-body images. Medical scan data representing one or more organs undergoing physiological process of the patient is acquired. The heart or circulatory system for the patient may have no or any pathology. The patient may be in any state (e.g., relaxed, standing, laying, and/or stressed) during the scan.

One or more medical scans may be used. The medical system may acquire scan data from a past scan of the patient. The different data used for training the model or application for a given patient may either be acquired at to represent the patient at one time or at different times. For example, past medical information and medical images of the patient are used in combination with the current medical information and/or images to get a comprehensive picture of the patient condition as well as how the condition has evolved. This information may be sampled in the training database, such as using mathematical models of disease progression, along with the information at a given time, or a combination of these approaches. Several sets of scan data may be used simultaneously in the system, such as scanning with different settings to represent different characteristics of the patient.

In act 22, the medical system optionally acquires other data for the patient. The data is obtained by access to a memory, loading from memory, or transfer through an interface device or network. For example, the data is obtained as part of a web-service to mine a medical records database. The other data is in one or more memories and/or from one or more sensors. The data is obtained from a computerized medical record, billing database, department records, picture archiving and communications system (PACS), a laboratory, or another source.

A machine-learned network may be trained or applied using a multitude of different sources of data. The machine learning algorithm and resulting machine-learned network use such information as the text in the clinical reports, medical images, medical scan data, biochemical information (e.g., blood biomarker, molecular, and/or genetic information), patient demographics (e.g., age, ethnicity, gender, weight, height, race, BMI, diabetes, hypertension, hypercholesterolemia, smoking history, family history of CAD, prior MI, prior PCI, prior CABG, angina type (stable/worsening/silent ischemia/other angina category, according to CCS, AHA/ACC) or others), patient history (e.g., smoking, alcohol consumption, high blood pressure, drug use, current medicines being used, or others), non-invasive measurements (e.g., blood pressure, heart rate, ECG signals, or others), patient state (e.g., stable or acute, relaxed or stressed, etc.), anatomical measures derived from the medical images, results of previously performed tests (e.g., exercise stress test), clinical history (e.g., radiation exposure), and/or information from other devices and sensors. The genomic or molecular information from the patient may include the presence of specific genomic markers. Molecular markers like miRNA, mRNA, proteomics, etc. may also be used. The model may use the results of physiological modeling using patient data as input (e.g. blood flow, electrophysiology, biomechanics quantities, or others).

The data is from a past examination of the patient (e.g., previous image, demographics, and patient history) and/or includes current information. For example, a previous examination provides some of the information. Symptoms being currently experienced are also obtained. Other current measurements, such as CT imaging and blood biomarkers, are obtained. Obtaining the same type of data from different times may show progression. These different types of information may be acquired at a single time point or at different time points. For example, features extracted from an MRI performed during a previous visit may be used to predict the measure of interest. Similarly, blood biomarkers (the same or different) may be acquired at different time points and used as features of the machine learning algorithm.

In act 10, the medical system extracts a set of features from the medical scan data and/or the other data. The feature extraction is performed by a medical imaging scanner or on another device, such as an imaging workstation. A processor performs the extraction with or without user input through a user interface. Requests, mining, or searching formatted for the source obtains the data.

The resulting list of values for the features is stored as part of the training database or is used for application of the machine-learned network.

The process of feature extraction from images is fully automated, semi-automated, manual, or a combination of thereof. Under a manual approach, anatomical or other features are input, annotated, or measured by a human operator or user. For example, an imaging scanner or workstation displays a dialog that the user can edit to insert the features. The image is used to determine the values for the features. As another example, the user traces on an image.

Under an automated extraction, the medical system calculates values for the features. Segmentation, thresholding, filtering, template matching, detection (e.g., machine learned detection), other image processing, or combinations thereof are used to extract values specific to anatomy represented in the scan data. Alternatively or additionally, Haar wavelets, steerable features, the intensity values without processing, or other features calculated across the scan data regardless of represented anatomy are used.

Features can also be extracted automatically as part of a deep learning model. In this context, the data is given directly to a deep learning network, which will automatically extract features and perform the machine-learning task in an end-to-end fashion. Similarly, for application, the data is input to the deep learned network, which applies convolution or other process to extract features used in other layers of the network.

In acts 24, 26, and 28, the medical system applies one or more machine-learned networks. The input of the extracted features from act 10 in act 24 results in the determination of the quantity in act 26 and the output for act 28. A processor inputs the features, applying the machine-learned network to the input features to determine the PV loop and/or other physiological quantity. This output is used to derive diagnosis, prognosis, and/or treatment (e.g., treatment recommendation). In other embodiments, the determination is of the diagnosis, prognosis, and/or treatment outcome as the output of the network.

In act 24, a machine, such as an image processor, applies the medical scan data, other data, or features from the medical scan data and/or other data to a machine-trained estimation network. The machine-trained estimation network is any now known or later developed network trained to output a quantity, such as a neural network or support vector machine. The machine learning is supervised, semi-supervised, or unsupervised. Some examples using supervised learning include regression, instance-based methods, regularization methods, decision tree learning, Bayesian, kernel methods, clustering methods, association rule learning, artificial neural networks, dimensionality reduction, and ensemble methods. Probabilistic boosting tree, hierarchal, or other processes may be used.

In one embodiment, the machine-trained estimation network is a deep learned network, such as a neural network. Such networks have a pool of shared layers to determine common features to the task at hand and additional layers that are trained for classification from the features.

Multiple networks may be used. For example, one or more machine learning algorithms may be used in a cascaded or parallel workflow. One network predicts one result. One network may be trained to predict multiple types of results. For example, the same network predicts two or more physiological quantities in a multi-task or cascaded architecture of layers or units. Alternatively, different networks are used for different physiological parameters.

Rather than training one network, the network may be learned as a network of different models, where each model works on some subset or the entirety of the feature space. The outputs from each model may be used as inputs to other models, thereby creating new features. The output from one model may be used as an input to the same model to produce recursive model estimates. The network may be trained to learn from categorical, discrete, and/or continuous features. The network may be a combination of multiple interacting machine-learned networks, each of which use the same or a different subset of features. The outputs from one model can be used as an input to another network.

Collecting a statistically significant number of training samples (e.g., thousands of patients with known results for a given condition or number of conditions) may be difficult. Many samples are desired for each unique pathology. Acquiring the samples from actual patients may be difficult, especially with known values of physiological parameters (e.g., PV loop) to use as ground truth in training. Some of the training data may be synthetically generated to fill any gaps, or the entirety of the training data is synthetically generated. It may be difficult to locate many samples of patients suffering from one or more conditions, combination of conditions, or specifics to a condition. Synthetic examples may be created. Rather than using specific existing patient cases for the training data, data not specific to an existing or previously handled patient is used. The synthetic sample is generated in-silico with a known outcome. An actual patient may be the starting point, but the modeling creates an anatomy representation and/or other data not specific to a given patient. A value of one or more parameters of the in-silico model are changed to create a different sample than provided by the actual patient. The machine-trained network is trained only from synthetic data or from a combination of data from a collection of patients and synthetic data.

The synthetic data may be for the other data and/or the medical scan data. In one embodiment, the synthetic data is of medical images or other medical scan data. The machine-trained network is trained from examples of scan data generated with computer modeling, physical modeling, or both computer and physical modeling using in vitro or in silico models and corresponding ground truths. A model is provided with different values of one or more parameters, resulting in different synthetic pathologies. An image simulator then simulates generation of one or more sets of scan data from each of the models. The resulting synthetic scan data samples are stored in a database. The values of the parameters, the synthetic data, and/or information derived therefrom (e.g., pathological condition being modeled) are stored in the database as the ground truth for the synthetic images.

Figure 3:
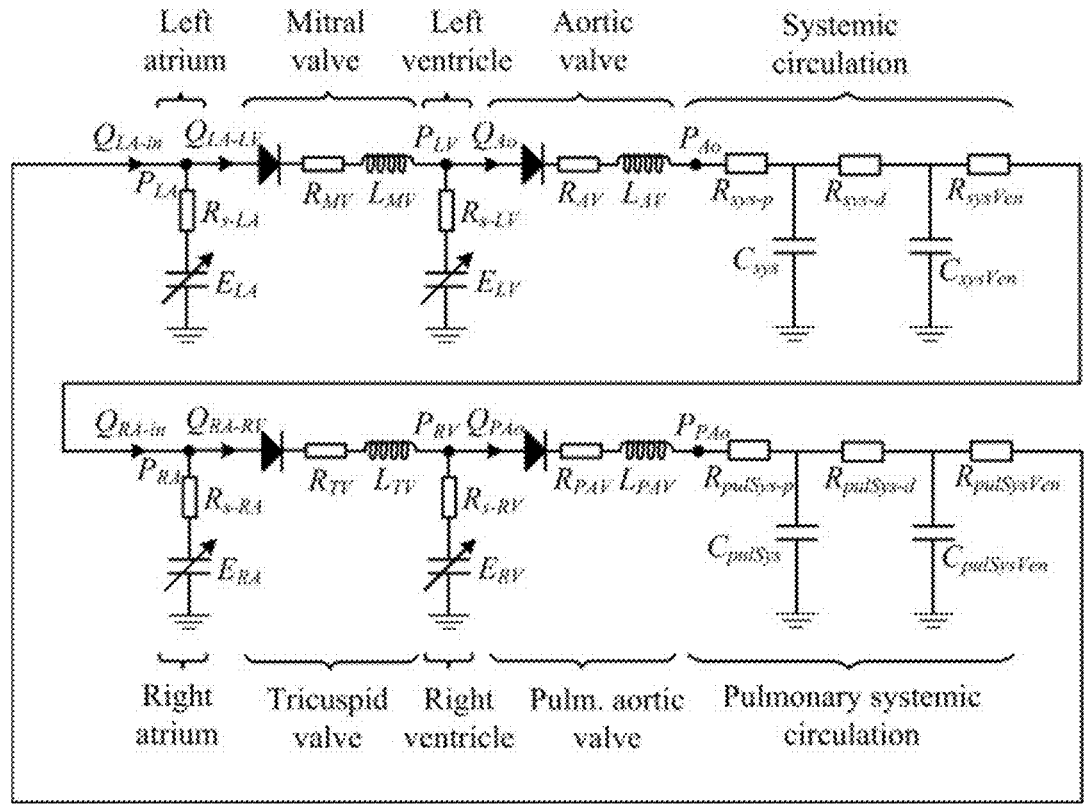
FIG. 3 illustrates an example lumped model of the circulatory system.

For each synthetic sample, the ground truth value of the physiological quantity is provided for training. Modeling may be used to determine the ground truth. For the cardiovascular system, FIG. 3 illustrates an example lumped parameter closed loop model. Other physiological models may be used, such as a 1D model, a 3D model, or a multiscale model (e.g., 3D for the LV and lumped for other parts of the cardiovascular system). The physiological model is employed to generate output measures of interest (e.g. PV loop, stroke work, etc.) for a large number of datasets. The lumped parameters model of FIG. 3 is a whole-body circulation model, but physiological models for a part of the cardiovascular system may be used.

Figure 4:
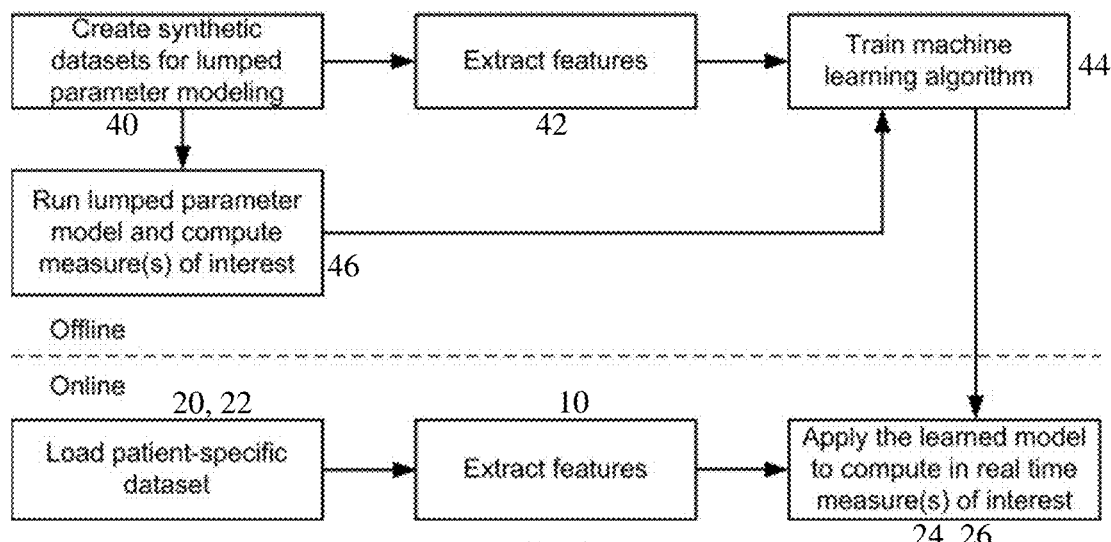
FIG. 4 is a flow chart diagram of an embodiment of a method of training with created synthetic data and application of the learned network for patient-specific physiological quantification.

FIG. 4 is a flow chart diagram of one embodiment of a method for training and real-time prediction. The application portion (e.g., acts 20-26) is discussed with respect to FIGS. 1 and 2. To train the network for application, acts 40-46 are performed. The training uses synthetically generated scan data and/or other data. Actual examples from patients may also be used to populate the database or no actual examples are used. The approach of using synthetic images and/or datasets has the advantage of being able to span pathological conditions that are relatively rare and hard to sample from the patient population in sufficient numbers. The large number of variations available is one benefit of using synthetic data for training. A very large number of samples can be automatically generated, leading thus to an extensive database. Complex pathological configurations can be generated. Since the generation of synthetic in-silico geometries can be completely automated, the cost of generating a large database is reduced. The samples may be generated for specific demographic groups easily. The training can be done in a global manner or a site-specific manner. This allows the system to account for anatomical trends based on patient demographics and epidemiology. The training can be iteratively improved with either more data or with better representations of the features.

The acts for training are performed in the order shown or a different order. Additional, different, or fewer acts may be used.

The method of FIG. 4 is implemented by a server (local or cloud-based), computer, or workstation as the medical system using physiological models. Any medical system for training a machine to determine physiological quantification may be used. The same or other medical system for application may be used.

For training, the extracted features and known ground truth (i.e., PV loop) for the samples of the training data are used to learn. The input feature vectors and corresponding results for many samples are used in machine learning. Tens, hundreds, or thousands of examples are used to train. Greater numbers of training examples may result in more reliable output. The corresponding feature values are used to map the feature values to the results. A large database based on patient-specific and/or synthetic data is used. Such a database should contain numerous pairs of input data sets (e.g. as acquired during trials or generated in silico) and the corresponding output measures of interest. These datasets may represent both healthy individuals and patients with various pathologies (valve disease, dilated cardiomyopathy, hypertrophic cardiomyopathy, hypertension, athletes, etc.) at different states (rest—baseline, different levels of exercise, etc.). Once a large database of pairs consisting of input data—output measures of interest is available, an artificial intelligence model is trained to predict the measures of interest.

In act 40, the medical system creates synthetic datasets for lumped parameter modeling. FIGS. 5A and 5B show the training as a two-step process for generating synthetic input data with the lumped parameter model of FIG. 3. In act 40, various parameters of the lumped parameter model are controlled, such as the parameters listed in FIG. 5A. Study-based variability or distribution of values may be used. Alternatively, a range for each value is defined and various combinations of any values being sampled are generated. Random sampling may be used.

In one embodiment, 3D computational models of anatomy are used. The anatomy model is generative, so any type of condition or pathology, at any time of the development process, and/or for any tissue or organ, accordingly, may be used to generate a synthetic 3D anatomy with known properties. Studies or other research may provide the computational model. The computational model is defined by parameters that control characteristics of the synthetic anatomy. Different pathology may be created by different values of the parameters. Synthetic datasets are created for various samples.

The mechanistic or computational model is represented by one or more equations. The equations for the mechanisms may include any spatial representation, such as solving in 3D using the finite element method as a series of partial differentiations. In additional or different embodiments, the mechanistic or computational model is or includes a machine-learned classifier. The anatomy model is learned using artificial intelligence approaches, such as multi-agent systems and deep reinforcement learning. Deep reinforcement learning techniques could be used to train the agents to directly achieve the end-point simulated by macroscopic models. The machine-learned model is trained from data from actual patients.

In act 42, the medical system extracts features. The other data or scan data is generated from the synthetic dataset. For example, a model of a medical scanner is used to generate scan data emulating a pathology as represented by the anatomy model. As another example, scan data from an actual patient with a similar pathology is altered to account for the change to create the synthetic sample. In yet another example, scan data is generated from a machine-learned GAN, as discussed below for FIG. 6. Alternatively, other data than scan data is created as the synthetic data. The training is to predict the quantity without scan data.

In act 46, the medical system generates the ground truth for each of the samples. For example, a PV loop is generated for each of the samples. The 3D or other anatomy models may be used to calculate the ground truth (e.g., PV loop). For each sample of synthetic data, a corresponding set of values for the anatomy model are provided. The anatomy model as configured by the values is used to calculate the quantity. For example, synthetic input data for training is generated by the lumped parameter model. The lumped parameter model, configured by the values of the parameters, generates one or more outputs. FIG. 5B shows an example of a LV volume as a function of time output by the lumped parameter model. Using a pressure curve over time from the lumped parameter model provides the PV loop.

Based on the values for the model parameters, the medical system models anatomy. Any mechanistic or computational modeling may be used. Rather than using anatomy from an actual patient, a model of the anatomy is used. In the example of FIGS. 5A and 5B and the lumped model of FIG. 3, non-imaging data is used. Rather than generate scan data as one of the features in act 42, the features are values of the parameters of the anatomy model (e.g., the lumped model) or other characteristics derived from the anatomy model. This allows a rule-based approach where non-imaging data is used as input for training and application.

FIG. 6 shows one embodiment of a method for training for synthetic data generation and training for quantification in a medical system for quantification. A GAN is used to generate the synthetic examples, including scan data (e.g., image data) and/or other data. The synthetic data includes the type of data for application to estimate a value for a physiological parameter. The method generates synthetic data for machine learning to estimate a physiological quantity, such as a PV loop.

Additional, different, or fewer acts may be used. For example, act 62 is not performed. As another example, acts for configuring the GAN architecture, selecting parameters, configuring the training, and/or using the trained GAN to generate synthetic data are provided.

In act 60, a machine (e.g., image processor) trains a GAN to generate synthetic data. Any GAN may be used. FIG. 7 shows an example GAN for generating synthetic data. Two neural networks form a generator network 72 and a discriminator network 74. The generator network 72 is optimized to fool the adversarially-trained discriminator network 74 into predicting that synthetic datasets are real. The discriminator network 74 is initially trained using patient-specific datasets 76 to discriminate between actual data 76 and synthetic data. The training process is iterative, i.e. the generator network 72 and the discriminator network 74 are trained iteratively. The generator network 72 learns to generate synthetic data that the discriminator network 74 cannot discriminate from actual patient data. The discriminator network 74 learns to discriminate even as the generator network 72 provides more realistic synthetic data. The result is a generator network 72 that may generate many samples of synthetic data that closely model a variety of real data.

The generator network 72 is seeded with a randomized input that is sampled from a predefined latent space (e.g. a multivariate normal distribution). The generator network 72 is trained to generate various instances of anatomy (e.g., scan data) and/or other data based on samples 76 of the anatomy and/or other data from actual patients being provided to the discriminator network 74 and feedback of a binary discrimination by the discriminator network 74.

The neural network of the generator network 72 is a convolutional, fully convolutional, and/or deconvolutional network. In one embodiment, a plurality of layers is used with further abstraction from one layer to the next. Another plurality of layers reduce abstraction to generate the synthetic data. A U-net or similar arrangement may be used.

The generator network 72 is trained to generate the synthetic data, such as medical images and/or other data. The synthetic data is not specific to any existing patient cases but is instead generated based on the latent space to emulate patient cases.

The generator network 72 may be trained to generate the synthetic data as well as the ground truth for the synthetic data. The GAN is trained to generate the synthetic data representing the various instances of the anatomy and to generate ground truth for each of the samples of the synthetic data. The ground truth for training in act 64 for estimating the value of the physiological parameter is generated. In training, the discriminator network 74 receives the synthetic data and ground truth from the generator network 72. The ground truth is also received as part of the patient-specific data 76, such as receiving a PV loop data from a physiological model (e.g., lumped model of FIG. 3) based on the patient specific data. To improve the performance of the GAN-based approach, not only the output of the generator network 72 may be used as input for the discriminator, but also the corresponding output measures of interest as generated by the physiological model of the cardiovascular system. Hence, the generator network 72 itself may not only generate the synthetic input datasets, but also the corresponding computed output measures of interest.

In one embodiment, the GAN is controllable by one or more discrete random variables. The variables parameterize one or more characteristics of the synthetic data, such as controlling values or distribution of values for one or more features (e.g., scan data or other data) and/or one or more outputs (e.g., PV loop). The characteristics of the synthetic data may be controllable. The condition represented by the synthetic data may be controlled.

The GAN is trained with the one or more variables to include this control. Rather than using just the latent space 70 as noise, one or more controlled variables are provided. For example, InfoGAN is used. Other more advanced type of GAN may be employed. For the GAN of FIG. 7, a simple factored continuous noise vector and/or matrix is used as input 70 and no further conditions are imposed on the way the generator network 70 uses the noise to generate a candidate. Using InfoGan, one or more discrete random variables may be used as input information to parameterize the features of the candidate or sample that is generated. As the discriminator network 74 uses this additional knowledge to classify the cases, the generator network 72 is forced to capture how the generator network 72 should change the produced geometry to still be able to fool the discriminator network 74. Thus, the training database of synthetic data is generated in a more controlled fashion. Since feature values are provided as additional input to the generator, datasets with the desired properties are produced. The training database and the distribution of samples over the features may be controllably created by selectively sampling geometries using the whole input feature space.

For example, the discrete variable characterizes vessel or cardiac pathology. The training of the GAN in act 60 uses control variables of the GAN. The GAN learns to use the variable to ensure that all relevant or desired types of vessels or cardiac structure are well enough represented in the training database. For example, many synthetic samples representing non-existent patients with HCM, DCM, hypertension, and/or other conditions are to be created through control of values of a variable provided as an input 70.

In act 62, one of more of the random variables are set to one or more values to control generation of the synthetic data. Based on a plan for the dataset, population studies, identification of conditions with a limited number of samples, and/or other information, the discrete random variables are controlled as a control on a distribution of conditions represented by the synthetic data. Based on the controlled variable or variables and other data (e.g., noise), the generator network 72 as trained generates many samples for each condition through repeated use.

In act 64, the machine trains a quantification network to infer a physiological quantity. The quantification network is trained based on the synthetic data from the GAN, the generative network 72 in particular. For example, a neural network is trained to estimate the PV loop based on input patient data (e.g., scan data and/or other data). In another example, the quantification network is trained to infer the physiological quantity based on the medical images. The training uses the ground truths for the various samples in the data base to learn to infer based on an unseen input. The samples, including the scan data, and corresponding ground truth are from, at least in part, synthetic generation by the machine-trained generator network 72.

The trained quantification network is stored for later use. The quantification network may be applied by a server, workstation, medical scanner, or other image processor for any number of patients. The trained quantification network is available for performing acts 26 and 28 of FIGS. 1 and 2. The GAN and/or generator network 72 are not used other than for generating training data for training the quantification network in act 64 but may be stored for generating further synthetic samples for training a different network and/or for retraining.

Once the quantitative network is deployed in a hospital or elsewhere, more clinical datasets from actual patients may become available. The quantitative network may be retrained. The retraining and/or initial training is performed centrally (e.g., off-site of a medical facility), locally (e.g., on-site at a medical facility such as a hospital), and/or in a distributed manner (e.g. using data from different clinical centers). Once the newly trained quantitative network or networks are available, these networks may be distributed to clinical sites for application to specific patients.

Returning to FIGS. 1 and 2, in act 26, the image processor determines a value for one or more physiological parameters by the application to the machine-trained estimation or quantification network. For example, the network outputs a PV loop for the patient based on the input of act 24. The network determines the output through convolution, deconvolution, pooling, weighting, links, and/or other relationships of the input to infer the output. The relationship between input data (e.g., the anatomy) and quantities of interest (e.g., PV loop) is represented by a model built from a database of samples with known characteristics and outcome.

Since a machine-learned network is used, the determination of act 26 occurs within milliseconds of the input of act 24. The input of act 24 may occur prior to and/or after completion of the scan to acquire scan data in act 20. As a result, the quantity (e.g., PV loop) for a given patient is determined within a second of the acquisition (e.g., completion of a medical imaging scan). Once the model is trained, its application to unseen data provides results almost instantaneously.

One or more of various physiological parameters may be determined. Values for various quantifications used for diagnosis, prognosis, treatment, and/or surgical planning may be provided. Any quantification of the cardiac system, for which the estimation network is trained to provide, may be provided. The measures of interest to be predicted by the machine learning algorithm may include time-varying pressure of the left and/or right ventricle (or any derived measure), the PV loop of the left and/or right ventricle, and/or a measure of the cardiovascular function of the patient (e.g., systolic systemic and/or pulmonary pressure at a certain location of the arterial tree, diastolic systemic and/or pulmonary pressure at a certain location of the arterial tree, end-diastolic volume, end-systolic volume, ejection fraction, stroke volume, left and/or right ventricular end-systolic pressure, left and/or right ventricular end-diastolic pressure, left and/or right ventricular end-systolic elastance, arterial compliance, dead volume of the left and/or right ventricle, left and/or right ventricular volume corresponding to a left ventricular pressure of 100 mmHg, proximal systemic and/or pulmonary resistance, distal systemic and/or pulmonary resistance, total systemic and/or pulmonary resistance, left and/or right ventricular stroke work, normalized left and/or right ventricular stroke work PV such as stroke work divided by stroke volume, arterial elastance such as computed as end systolic pressure divided by stroke volume, and/or arterial ventricular coupling such as arterial elastance divided by left ventricular end-systolic elastance). Other quantities may be determined.

Figure 8:
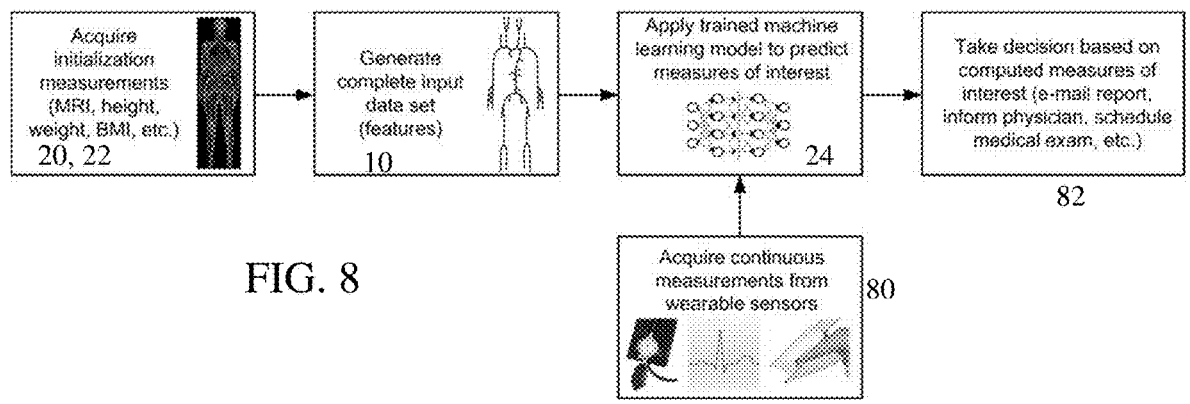
FIG. 8 is a flow chart diagram of one embodiment of a method for physiological quantification based on data from wearable sensors.

FIG. 8 shows another embodiment for input in act 24 of FIG. 1 to a machine-learned quantification network. The machine-learned network is trained to use, at least in part, data from one or more wearable sensors. The quantification is used to determine patient evolution and/or make a clinical decision for the patient. The evolution may be more accurately predicted due to providing periodic or on-going measures from a wearable sensor. A machine learning model may learn to predict the patient evolution. Such a model may use data 80 provided by wearable measurement systems, such as body area networks and/or sensors.

In acts 20 and/or 22, a set of initialization measurements are performed. These initial measurements may be based on medical imaging, like MRI, CT, angiography, echocardiography or only on more basic measurements like height, weight, BMI, etc. of the subject. These measurements are used to build an initial complete set of input data (features) in act 10. Next, continuous or periodic measurements 80 are acquired from the wearable sensor network. These measurements 80 may include quantities like heart rate, blood pressure, pulse oximetry measurements, ECG, etc. These measurements 80 are used together with the previously defined set of input data as input features to the machine-learned estimation network for predicting in act 26 one or more measures of interest.

The extracted measures of interest may be sent to the patient (phone, e-mail, etc.) and/or to a physician. A recommendation for a clinical investigation may be issued in act 82. Hence, this methodology may allow for a paradigm shift from mainly reactive medicine to more predictive medicine, where the patient is treated before the disease reaches a high or critical level of severity. This in turn may not only improve the patient outcome, but also lead to reduced healthcare related costs.

The machine-learned model may be run either locally to the patient or physician or the acquired data may be sent by wired and/or wireless communication to a central server (cloud) where the processing may be performed.

Figure 9:
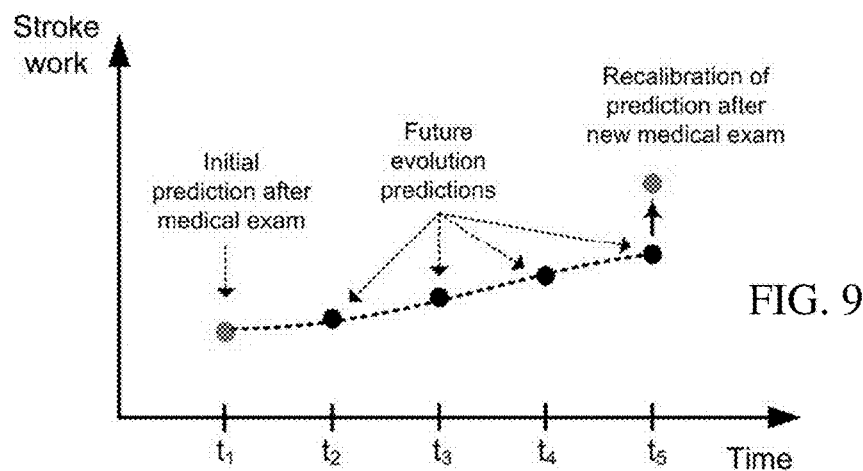
FIG. 9 illustrates prediction of evolution of a physiological quantification over time.

In another embodiment, the measures of interest may be predicted only at the time of the medical exam, and a separate machine-learned model may be employed to predict the patient evolution. The training of a network to predict evolution may require a large patient-specific database including information of past patient or synthetic evolutions. For example, such a model may use as input features, amongst others, the time of the medical exam and a future timepoint for which the model should predict a certain quantity of interest. A graph, as depicted in FIG. 9 may be obtained. FIG. 9 shows prediction of the evolution of stroke work for a patient over at least four time points in the future based on the current time, $t_1$. Predictions of the evolution of other quantities may be provided, such as of the PV loop for a patient. Once or if the patient is examined at some point in future, a new complete input dataset may be available, and the prediction may be recalibrated.

Where multiple quantities are determined and/or where multiple networks are applied for different purposes, the system may be implemented as a multi-task neural network. For example, a multi-task network may predict both values of measures of interest and their future evolution. Such networks typically have a pool of shared layers to determine common features to the task at hand and additional layers that are trained for the specific tasks. Alternatively, cascaded, parallel, or separate networks may be used.

In act 28 of FIGS. 1 and 2, the image processor outputs the determined quantity or quantities. The output is on a display, such as showing an anatomical image rendered from scan data with a notation providing the quantity as alpha-numeric text, a graph, or chart (e.g., the graph of FIG. 9 is output). The output image may be of a medical report with quantity included. Other outputs to a memory and/or transfer over a computer network may be provided.

In act 29, the image processor uses the determined value for the quantity or values for the quantities. The value or values may be used as inputs to another machine-learned network. For example, the further network is trained to determine the evolution from, in part, the value of the quantity. As another example, the value or values are all of or part of an input feature vector to a machine-learned network for clinical decision support. The network is trained to output a clinical decision based on the value or values with or without scan data and/or other data.

In an example decision support system, a machine learning algorithm is trained to predict the "clinical decision", rather than a measure of interest like the PV loop or stroke work. Any of the above-mentioned features and measures of interest may be used as input features for determining the clinical decision, including any anatomical measures extracted from the medical images, and the output of any type of machine-learned estimation network of measures of interest. This provides for a cascade of machine-learned networks. A multi-task network may be used instead.

The machine-learned decision support network outputs a clinical decision in response to the input feature vector. The measure of interest to be predicted by the machine learning algorithm is a clinical decision. For example, a recommendation to send the patient for invasive and/or non-invasive testing, prescribe medical therapy, prescribe medication, prescribe home treatment, and/or other clinical decision is output based training data and ground truth from examples of best outcomes. The clinical decision may be a binary decision, such as (1) schedule the patient for a cathlab (e.g., further non-invasive and/or invasive testing and/or intervention) or (2) do not send the patient to the cathlab. The clinical decision may be a continuous variable, like the date of a future screening exam. In another embodiment, the clinical decision may be a series of hierarchical decisions, such as: (1) schedule the patient for further non-invasive and/or invasive testing and/or intervention or (2) do not send the patient to the cathlab, but (2a) discharge the patient and prescribe medication or (2b) discharge the patient and do not prescribe any medication.

Alternatively, in case of more than two options, a multiple option choice may be performed (e.g. using a multi-class classifier). Each decision may be followed by more fine-grade options of that decision. If the decision is to send the patient home, the machine-learned model may be further employed to decide which type of medication should be prescribed and when should the patient return for a follow-up and/or screening exam.

The machine-learned network may produce results ("clinical decision" or quantity) either as an absolute value (with probability=1), or as a set of probabilities for each decision. For example, the result could be: (1) schedule the patient for a cardiac CT exam—probability→0.95 and (2) do not schedule the patient for a cardiac CT exam: Probability→0.05. Instead of taking a specific decision, the machine-learned decision support network may be used to present to the user the top n (e.g. 3) possible decisions, ranked based on their corresponding confidence. The user may then take the final decision.

The clinical decisions may be defined at patient level or at anatomical structure level (e.g. left ventricle, right ventricle, etc.). The clinical decisions may be visualized, either as text or in a graphical way (e.g. overlaid on the medical images), and presented to the clinician.

The machine-learned network or networks may operate automatically. In an alternative embodiment, the user and/or clinician intervenes, leading to a semi-automated decision-making method. For example, the clinician may select a subset of decisions that are appropriate (e.g., a certain type of invasive test may not be available in the hospital) from a large set of possible decisions. Hence, machine-learned network may then output a clinical decision from the group of selected or appropriate decisions. Multiple machine-learned networks may be trained for different subsets of possible decisions, or the same machine-learned network may be employed irrespective of the selected viable decisions, and the one with highest probability from the selected set may finally be suggested. Alternatively, the clinician may intervene in the workflow by choosing to discard some of the input information and/or features that are considered irrelevant or inaccurate. Where the network uses such input, population-based, demographic-based, or default values may be used instead.

The machine-learned decision support network may be used to guide decision making under emergency conditions or for triage. In case of multiple patients requiring decision making in the emergency department, a trained machine learning algorithm may be employed to determine the order in which to see the patients and/or schedule the exams. The machine learning may use as input information prior exams of the patient, current symptoms, similar patients from the past, and/or other information with or without imaging data.

Separate machine learning algorithms may additionally be employed to provide confidence intervals for the estimation of different measures of interest. Since such machine learning algorithms also require large training databases, in an advantageous embodiment, the database would be composed of synthetic data, but a database containing synthetic and patient-specific data may be likewise used.

FIG. 10 shows a medical system for training and/or application of a machine-learned classifier for physiological quantification. The medical system includes a medical imaging system 11, an image processor 13, a memory 15, and a display 16. The image processor 13 and the memory 15 are shown separate from the medical imaging system 11, such associated with being a computer or workstation apart from the medical imaging system 11. In other embodiments, the image processor 13 and/or memory 15 are part of the medical imaging system 11. In alternative embodiments, the medical system is a workstation, computer, or server. For example, the medical imaging system 11 is not provided or is provided for acquiring data representing a volume, and a separate database, server, workstation, and/or computer is provided for extracting features and applying a network to provide one or more results. Additional, different, or fewer components may be used.

The system is used for application of a machine-learned model (e.g., one or more machine-learned networks). In alternative embodiments, the system is used for training with machine learning and/or generation of the examples in the database. Where only synthetic samples are used, the medical imaging system 11 may not be provided for generating the database of training data. Where the samples of the training data, even if from actual patients (e.g., scan data representing actual scans), are stored in the memory 15, the medical imaging system 11 may not be provided.

The computing components, devices, or machines of the medical system, such as the medical imaging system 11 and/or the image processor 13 are configured by hardware, software, and/or firmware to perform any of the acts. The computing components operate independently or in conjunction with each other to perform any given act, such as the acts of any of the methods described above. The act is performed by one of the computer components, another of the computing components, or a combination of the computing components. Other components may be used or controlled by the computing components to scan or perform other functions.

The medical imaging system 11 is any now known or later developed modality configurable to scan a patient. The medical imaging system 11 scans the patient. For example, a C-arm x-ray system (e.g., DynaCT from Siemens), CT like system, or CT system is used. Other modalities include MR, x-ray, angiography, fluoroscopy, PET, SPECT, or ultrasound. The medical imaging system 11 is configured to acquire the medical imaging data representing the patient. The scan data is acquired by scanning the patient using transmission by the scanner and/or by receiving signals from the patient.

The memory 15 is a buffer, cache, RAM, removable media, hard drive, magnetic, optical, database, or other now known or later developed memory. The memory 15 is a single device or group of two or more devices. The memory 15 is within the system 11, part of a computer with the image processor 13, or is outside or remote from other components.

The memory 15 is configured to store medical scan data, other data, extracted features, examples (e.g., training data or data from other patients), and/or other information. Output results, information derived from the results, or calculations used to determine the results are stored in the memory 15. The memory 15 stores one or more matrices, convolution kernels, and/or other representation of the machine-learned network or networks.

The memory 15 is additionally or alternatively a non-transitory computer readable storage medium with processing instructions. The memory 15 stores data representing instructions executable by the programmed image processor 13 and/or medical imaging system 11. The instructions for implementing the processes, methods and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The image processor 13 is a general processor, digital signal processor, three-dimensional data processor, graphics processing unit (GPU), application specific integrated circuit, field programmable gate array, digital circuit, analog circuit, combinations thereof, or other now known or later developed device for processing data. The image processor 13 is a single device, a plurality of devices, or a network. For more than one device, parallel or sequential division of processing may be used. Different devices making up the image processor 13 may perform different functions, such as extracting values for features by one device and applying a machine-learned network by another device. In one embodiment, the image processor 13 is a control processor, GPU, or other processor of the medical imaging system 11. The image processor 13 operates pursuant to stored instructions to perform various acts described herein.

The processor 13 is configured to apply information from a medical imaging scan to a machine-learned network. The machine-learned network is configured by training to output a pressure volume loop and/or other quantity in response to the application of the information. In one embodiment, the machine-learned network is trained with synthetic data. Samples not representing specific patients are generated by perturbing a physiological model of the anatomy. The resulting quantities for the perturbed model, scan data simulated or estimated for the anatomy model, and/or other data simulated or estimated for the anatomy model are stored in a database. The perturbation is controlled or randomly sampled to create many samples for training. Once trained, the application of input features to the network provides an output in real-time with the scan. Within a second of completion of a scan of a patient and/or entry of data to the network, the quantity or quantities of interest are estimated by the machine-trained network.

The display 16 is a CRT, LCD, plasma, projector, printer, or other output device for showing an image. The display 16 displays the results or information derived from the results. For example, a PV loop is displayed with or without an image or sequence of images of anatomy or flow for the patient. Probabilities associated with any prediction, supporting data (e.g., values of input features), images from the medical scan data, and/or other information may be output to assist the physician.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for physiological quantification in a medical system, the method comprising:

acquiring medical scan data representing anatomy of a patient;

applying, by a machine, the medical scan data or features from the medical scan data to a machine-trained estimation network, the machine-trained estimation network having been trained, at least in part, from synthetic data generated by a generator of a machine-trained generative adversarial network, the synthetic data not specific to existing patient cases;

determining, by the application to the machine-trained estimation network, a pressure-volume loop for the patient, the pressure-volume loop determined within a second of the acquisition of the medical scan data; and outputting the pressure-volume loop.

2. The method of claim 1 wherein acquiring comprises acquiring computed tomography data, magnetic resonance data, or molecular imaging data, and further comprising acquiring other patient information for the patient, the other patient information being other measures, a state, test results, biochemical information, demographic information, and/or clinical history, wherein the other patient information or features from the other patient information are applied to the machine-trained estimation network with the medical scan data or features from the medical scan data.

3. The method of claim 1 wherein the machine-trained estimation network comprises a deep learned network, and wherein determining comprises determining by the deep learned network.

4. The method of claim 1 wherein determining comprises determining the pressure-volume loop and a value of another quantification of a cardiac system of the patient.

5. The method of claim 1 wherein applying comprises applying to the machine-trained estimation network having been trained from the synthetic data generated by the generator of the machine-trained generative adversarial network constrained by a discrete variable characterizing a condition.

6. The method of claim 5 wherein the machine-trained generative adversarial network (GAN) constrained by the discrete variable comprises an infoGAN.

7. The method of claim 5 wherein the discrete variable characterizes cardiac pathology.

8. The method of claim 1 wherein applying comprises applying to the machine-trained estimation network having been trained from the synthetic data generated by the generator of the machine-trained generative adversarial network, the machine-trained generative adversarial network comprising the generator and a discriminator, the discriminator receiving the synthetic data and ground truth from the generator and a pressure-volume loop data from a physiological model.

9. The method of claim 1 wherein determining comprises determining a prediction of an evolution of the pressure-volume loop for the patient.

10. The method of claim 9 wherein applying comprises applying data from a patient wearable sensor to the machine-trained estimation network.

11. The method of claim 9 wherein determining the prediction and the pressure-volume loop comprises determining with the machine-learned estimation network being a multi-task neural network.

12. The method of claim 1 further comprising inputting the pressure-volume loop or a feature from the pressure-volume loop to a machine-learned decision support network, the machine-learned decision support network outputting a clinical decision in response to the inputting.

13. The method of claim 1 wherein outputting comprises displaying the pressure-volume loop and an image of the anatomy of the patient.

14. A method for machine training for synthetic data generation in a medical system for quantification, the method comprising:

training, by a machine, a generative adversarial network to generate synthetic data by a generator representing various instances of anatomy based on a plurality of samples of anatomy of patients and feedback from a discriminator; and training, by the machine, a quantification network to infer a physiological quantity, the quantification network trained based on the synthetic data from the generative adversarial network.

15. The method of claim 14 wherein training the generative adversarial network comprises training to generate the synthetic data as medical images, and wherein training the quantification network comprises training the quantification network to infer the physiological quantity based on the medical images.

16. The method of claim 14 wherein training the generative adversarial network comprises training the generative adversarial network with one or more discrete random variables parameterizing characteristics of the synthetic data, and further comprising controlling the discrete random variables as a control on a distribution of conditions represented by the synthetic data.

17. The method of claim 14 wherein training the generative adversarial network comprises training the generative adversarial network to generate the synthetic data representing the various instances of the anatomy and to generate ground truth for each of the samples of the synthetic data, wherein training the quantification network comprises training based on the synthetic data and the ground truth.

18. A system for physiological quantification, the system comprising:

a medical imaging scanner configured to scan a patient;

an image processor configured to apply information from the scan to a machine-learned network, the machine-learned network configured by training to output a pressure volume loop in response to the application of the information, the output being in real time with the scan, wherein the machine-learned network having been trained with data generated by perturbing a physiological model; and a display configured to display the pressure volume loop.

19. The system of claim 18 wherein the output being in real time comprises within a second of completion of the scan.

20. The system of claim 18 wherein the data represents anatomy and is generated by perturbing the physiological model of the anatomy.

* * * * *